(12) United States Patent
Takimura et al.

(10) Patent No.: US 8,389,685 B2
(45) Date of Patent: Mar. 5, 2013

(54) VECTOR ENCODING A PLASMID REPLICATION PROTEIN AND USE THEREOF

(75) Inventors: Yasushi Takimura, Haga-gun (JP); Yoshifumi Izawa, Wakayama (JP); Nobuyuki Sumitomo, Haga-gun (JP)

(73) Assignee: Kao Corporation, Tokyo (JP)

( * ) Notice: Subject to any disclaimer, the term of this patent is extended or adjusted under 35 U.S.C. 154(b) by 286 days.

(21) Appl. No.: 12/934,395

(22) PCT Filed: Mar. 24, 2009

(86) PCT No.: PCT/JP2009/056430
§ 371 (c)(1),
(2), (4) Date: Sep. 24, 2010

(87) PCT Pub. No.: WO2009/119876
PCT Pub. Date: Oct. 1, 2009

(65) Prior Publication Data
US 2011/0021751 A1    Jan. 27, 2011

(30) Foreign Application Priority Data

Mar. 25, 2008 (JP) ................................. 2008-078080

(51) Int. Cl.
| | |
|---|---|
| C07K 1/00 | (2006.01) |
| C12N 1/00 | (2006.01) |
| C12N 1/20 | (2006.01) |
| C12N 15/00 | (2006.01) |
| C12P 21/06 | (2006.01) |
| C12P 19/34 | (2006.01) |
| C07H 21/04 | (2006.01) |

(52) U.S. Cl. ...................... 530/350; 435/243; 435/252.3; 435/320.1; 435/69.1; 435/91.1; 536/23.1; 536/23.2

(58) Field of Classification Search .................. 530/350; 435/243, 252.3, 320.1, 69.1, 91.1; 536/23.1, 536/23.2
See application file for complete search history.

(56) References Cited

U.S. PATENT DOCUMENTS

| | | | | |
|---|---|---|---|---|
| 6,703,492 | B1 * | 3/2004 | Kimmerly ...................... | 536/23.1 |
| 7,364,891 | B2 * | 4/2008 | Hakamada et al. ............ | 435/209 |
| 7,563,611 | B2 * | 7/2009 | Tohata et al. ............... | 435/252.3 |

FOREIGN PATENT DOCUMENTS

| | | |
|---|---|---|
| JP | A-01-273591 | 11/1989 |
| JP | A-06-327480 | 11/1994 |
| JP | A-2000-287687 | 10/2000 |
| JP | A-2003-009863 | 1/2003 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Luthje et al., Identification and characterization of nine novel types of small staphylococcal plasmids carrying the linosamide nucleotidyltransferase gene Inu(A). J. Antimicrobial Chemotherapy., 2007, vol. 59: 600-606.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Written Opinion and International Search Report for PCT/JP2009/056430, mailed Aug. 7, 2009, from the European Patent Office, Munich, Germany.
Geneseq Database accession No. ADH00991, Plasmid pMM1520 repU protein #1, Mar. 11, 2004, revised Jun. 15, 2007, retrieved from EBI accession No. GSP:ADH00991.
Geneseq Database accession No. AAQ05037, Sequence encoding bacterial shuttle vector, Oct. 25, 1990, revised Mar. 10, 2003, retrieved from EBI accession No. AAQ05037.
EMBL Database (online) accession No. E02373, "Fragment DNA containing *Streptococcus faecalis* replication starting region," Oct. 7, 1997, last updated Nov. 9, 2005, retrieved from EBI accession No. EMBL:E02373.
Kirimura, K, et al., "Determination of nucleotide sequence related to the plasmid replication region in *Enterococcus faecalis* and its application to a new shuttle vector," *J Biosci Bioeng* 87(5): 566-571 (Jan. 1999), Society for Bioscience and Bioengineering, Japan.
Tian W et al., "How well is enzyme function conserved as a function of pairwise sequence identity?" J Mol Biol, Oct. 2003; 333(4): 863-882, Elsevier Ltd., Amsterdam, Netherlands.

* cited by examiner

*Primary Examiner* — Ganapathirama Raghu
(74) *Attorney, Agent, or Firm* — Sterne, Kessler, Goldstein & Fox P.L.L.C.

(57) ABSTRACT

To provide a plasmid vector having high productivity which can be used for large scale production of an industrially valuable and useful protein, and a transformant using the plasmid vector. A plasmid vector having DNA which encodes a plasmid replication protein in which one or more amino acid residues that are selected from (a) position 48, (b) position 262, (c) position 149 and (d) position 198 in the amino acid sequence represented by SEQ ID NO: 2 are substituted with (a) Ala, Gly, Thr, Arg, Glu, Asn or Gln, (b) Gly, Ser, Thr, Cys or Val, (c) Asn, and (d) Glu, respectively.

12 Claims, 1 Drawing Sheet

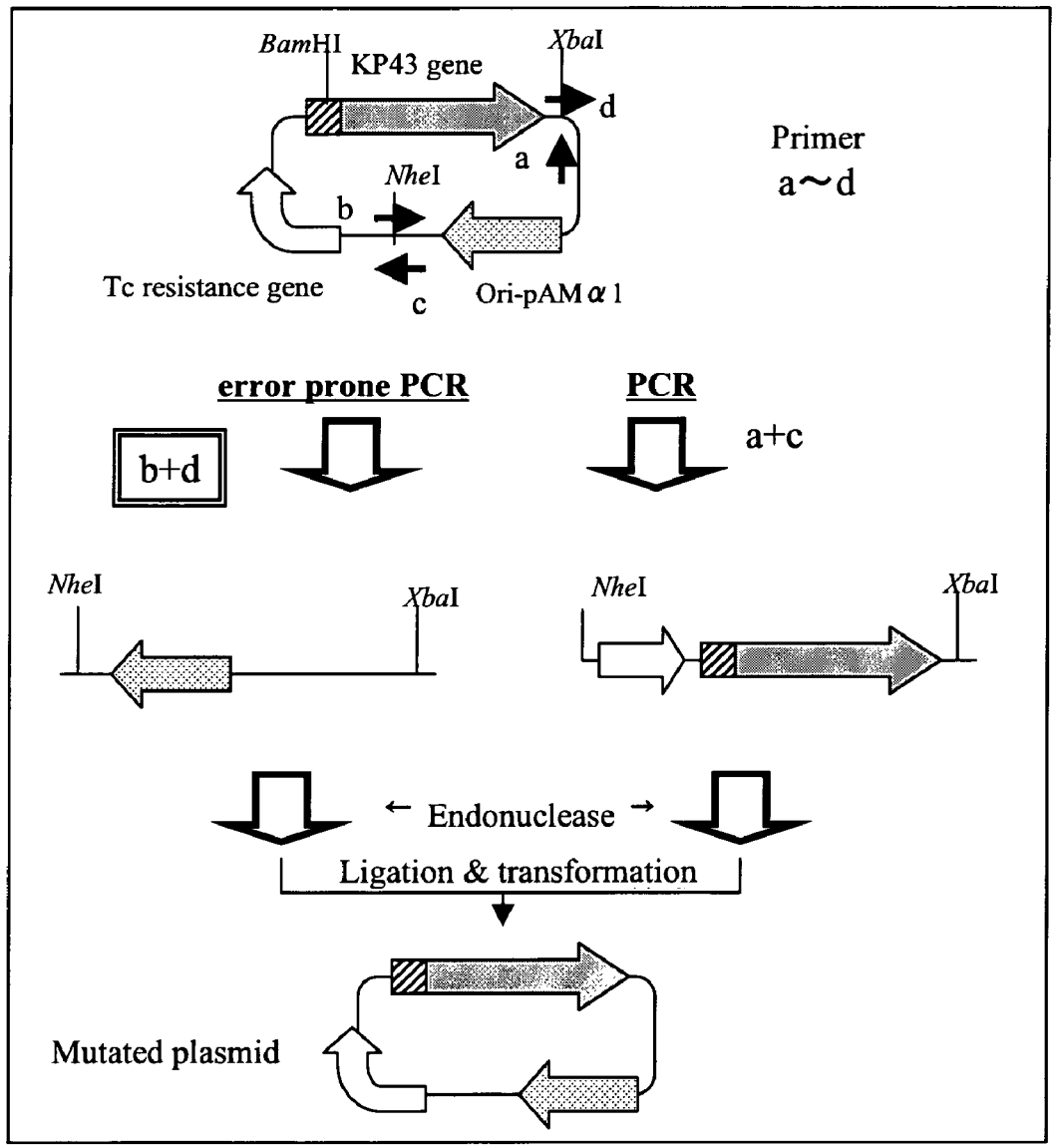

US 8,389,685 B2

VECTOR ENCODING A PLASMID REPLICATION PROTEIN AND USE THEREOF

REFERENCE TO SEQUENCE LISTING SUBMITTED ELECTRONICALLY

The content of the electronically submitted substitute sequence listing, file name: 25370380000Sequence_Listing_ascii.txt; size: 48,888 bytes; and date of creation: Sep. 24, 2010, filed herewith, is incorporated herein by reference in its entirety.

FIELD OF THE INVENTION

The present invention relates to a plasmid vector which contains a gene encoding a replication protein useful for producing a heterologous protein.

BACKGROUND OF THE INVENTION

In recent years, studies on genetic engineering have been actively carried out and there have been reported many techniques for producing useful proteins in large scale by using a recombinant microorganism. As one example of producing protein in a high amount, development of a plasmid vector with high productivity can be mentioned. For example, there are an expression and secretion vector in which various promoter regions of genes that are related to production of an extracellular enzyme such as amylase, protease, or levansucrase and a region encoding a signal peptide that is related to extracellular secretion of these proteins are included (Patent Document 1 and Patent Document 2), a vector whose replication region is modified to increase copy number thereof (Patent Document 3 and Patent Document 4) and the like.

However, according to the generally employed method for producing a protein based on a host vector system, the amount of protein production is not enough. In addition, types of proteins that can be produced in a high amount are also limited.

Prior Art Literatures
[Patent Document 1] JP-A-01-273591
[Patent Document 2] JP-A-2000-287687
[Patent Document 3] JP-A-06-327480
[Patent Document 4] JP-A-2003-9863

SUMMARY OF THE INVENTION

The present invention is directed to the following 1) to 11).
1) A plasmid vector containing DNA which encodes a plasmid replication protein, wherein the replication protein contains substitution of one or more amino acid residues that are selected from (a) position 48, (b) position 262, (c) position 149 and (d) position 198 in the amino acid sequence represented by SEQ ID NO: 2 with the following amino acid residue;
  (a) position: Ala, Gly, Thr, Arg, Glu, Asn or Gln
  (b) position: Gly, Ser, Thr, Cys or Val
  (c) position: Asn
  (d) position: Glu.
2) A plasmid vector containing DNA which encodes a plasmid replication protein, wherein the replication protein contains substitution of one or more amino acid residues that are selected from the amino acid residues present at positions corresponding to each of (a) position 48, (b) position 262, (c) position 149 and (d) position 198 of SEQ ID NO: 2 in an amino acid sequence having at least 800 identity to the amino acid sequence represented by SEQ ID NO: 2 with the following amino acid residue;
  (a) position: Ala, Gly, Thr, Arg, Glu, Asn or Gln
  (b) position: Gly, Ser, Thr, Cys or Val
  (c) position: Asn
  (d) position: Glu.
3) The plasmid vector of the above 1) or 2), further containing a nucleotide sequence of a promoter region and a secretory signal region of a gene which encodes alkaline cellulase derived from a microorganism belonging to *Bacillus* spp.
4) The plasmid vector of the above 3), wherein the nucleotide sequence of a promoter region and a secretory signal region of a gene which encodes alkaline cellulase derived from a microorganism belonging to *Bacillus* spp. is a nucleotide sequence of base numbers 1 to 659 of cellulase gene which consists of a nucleotide sequence represented by SEQ ID NO: 13, a nucleotide sequence of base numbers 1 to 696 of cellulase gene which consists of a nucleotide sequence represented by SEQ ID NO: 14, a nucleotide sequence having at least 701 identity to any one of the nucleotide sequences, or a nucleotide sequence in which part of the nucleotide sequence is deleted.
5) A transformant containing the plasmid vector of the above 4).
6) The transformant of the above 5), wherein a host of the vector is a microorganism.
7) A method for producing a polypeptide including the steps of:
  constructing a plasmid vector containing DNA which encodes a target polypeptide and DNA which encodes a plasmid replication protein, wherein the replication protein contains substitution of one or more amino acid residues that are selected from (a) position 48, (b) position 262, (c) position 149 and (d) position 198 in the amino acid sequence represented by SEQ ID NO: 2 with the following amino acid residue,
  (a) position: Ala, Gly, Thr, Arg, Glu, Asn or Gln
  (b) position: Gly, Ser, Thr, Cys or Val
  (c) position: Asn
  (d) position: Glu;
  transforming a host microorganism with the plasmid vector; and
  culturing the host microorganism and collecting the target polypeptide produced therefrom.
8) A method for producing a polypeptide including the steps of:
  constructing a plasmid vector containing DNA which encodes a target polypeptide and DNA which encodes a plasmid replication protein, wherein the replication protein contains substitution of one or more amino acid residues that are selected from the amino acid residues present at positions corresponding to each of (a) position 48, (b) position 262, (c) position 149 and (d) position 198 of SEQ ID NO: 2 in an amino acid sequence having at least 80% identity to the amino acid sequence represented by SEQ ID NO: 2 with the following amino acid residue,
  (a) position: Ala, Gly, Thr, Arg, Glu, Asn or Gln
  (b) position: Gly, Ser, Thr, Cys or Val
  (c) position: Asn
  (d) position: Glu;
  transforming a host microorganism with the plasmid vector; and
  culturing the host microorganism and collecting the target polypeptide produced therefrom.
9) The method of the above 7) or 8), wherein the plasmid vector further contains a nucleotide sequence of a promoter region and a secretory signal region of a gene which encodes alkaline cellulase derived from a microorganism belonging to *Bacillus* spp.

10) The method of the above 9), wherein the nucleotide sequences of a promoter region and a secretory signal region of a gene which encodes alkaline cellulase derived from a microorganism belonging to *Bacillus* spp. is a nucleotide sequence of base numbers 1 to 659 of cellulase gene which consists of a nucleotide sequence represented by SEQ ID NO: 13, a nucleotide sequence of base numbers 1 to 696 of cellulase gene which consists of a nucleotide sequence represented by SEQ ID NO: 14, a nucleotide sequence having at least 70% identity to any one of the nucleotide sequences, or a nucleotide sequence in which part of the nucleotide sequence is deleted.

11) A polypeptide which is produced according to the method of the above 7) or 8).

BRIEF DESCRIPTION OF THE DRAWING

FIG. 1 shows one example of constructing the plasmid vector of the present invention.

DETAILED DESCRIPTION OF THE INVENTION

The present invention provides a plasmid vector with high productivity for large scale production of an industrially valuable and useful protein, and a transformant using the same.

The present inventors have studied the large scale production of a protein through a modification of a plasmid, and have found that, by introducing a certain mutation into a replication protein of pAMα1, that is generally used as an replication origin region of plasmid (Rep), an extracellular secretion amount of protein produced from a structural gene of a target protein included in the plasmid is increased, and that such plasmid is useful for large scale production of a protein.

According to the plasmid vector of the present invention, extracellular secretion amount of a target protein, which is produced from a structural gene of the target protein included in the plasmid, is increased. As such, by using the plasmid vector of the present invention, a target protein can be efficiently produced.

The DNA, which is included in the plasmid vector of the present invention and encodes a plasmid replication protein, encodes the following protein (i) or (ii).

(i) A protein containing substitution of one or more amino acid residues that are selected from (a) position 48, (b) position 262, (c) position 149 and (d) position 198 in the amino acid sequence represented by SEQ ID NO: 2 with the following amino acid residue of (a) to (d);
    (a) position: Ala, Gly, Thr, Arg, Glu, Asn or Gln
    (b) position: Gly, Ser, Thr, Cys or Val
    (c) position: Asn
    (d) position: Glu.

(ii) A protein containing substitution of one or more amino acid residues that are selected from the amino acid residues present at positions corresponding to each of (a) position 48, (b) position 262, (c) position 149 and (d) position 198 of SEQ ID NO: 2 in an amino acid sequence having at least 80% identity to the amino acid sequence represented by SEQ ID NO: 2 with the following amino acid residue of (a) to (d);
    (a) position: Ala, Gly, Thr, Arg, Glu, Asn or Gln
    (b) position: Gly, Ser, Thr, Cys or Val
    (c) position: Asn
    (d) position: Glu.

As for a protein having an amino acid sequence represented by SEQ ID NO: 2, replication protein of plasmid pAMα1 from *Enterococcus faecalis* can be mentioned.

As for a plasmid replication protein which consists of an amino acid sequence having at least 80% identity to the amino acid sequence represented by SEQ ID NO: 2, a protein having an amino acid sequence different from the amino acid sequence represented by SEQ ID NO: 2 but having at least 80%, preferably at least 90%, more preferably at least 95% identity, still more preferably at least 98% identity to the amino acid sequence represented by SEQ ID NO: 2 can be mentioned.

Examples of the plasmid replication protein include those having one or more deletion, substitution, or addition of amino acids compared to the amino acid sequence represented by SEQ ID NO: 2. Specific examples include a replication protein from *Staphylococcus saprophyticus*. Among these, those having a capacity of self-cloning, such as the plasmid replication protein consisting of the amino acid sequence represented by SEQ ID NO: 2, are preferable.

The plasmid replication protein of the present invention means a protein having an amino acid sequence represented by SEQ ID NO: 2 or an amino acid sequence with at least 80% identity thereto, wherein one or more amino acid residues selected from the amino acid residue at (a) position 48 or a corresponding position, (b) position 262 or a corresponding position, (c) position 149 or a corresponding position, and (d) position 198 or a corresponding position are substituted with other amino acid residues. The plasmid replication protein of the present invention can be a wild type, or a naturally-occurred variant or an artificially mutated variant thereof.

In addition, sequence identity of an amino acid is calculated based on Lipman-Pearson method (Science, 227, 1435, (1985)). Specifically, by using a search homology program of genetic information processing software Genetyx-Win (Ver.5.1.1; Software Development, Co., Ltd.), analysis is carried out for the calculation, with ktup (unit size to compare) being set to 2.

Therefore, the plasmid replication protein of the present invention include: a protein having an amino acid sequence wherein the amino acid residue at position 48 (Lys residue) of the amino acid sequence represented by SEQ ID NO: 2 is substituted with Ala, Gly, Thr, Arg, Glu, Asn or Gln residue, the amino acid residue at position 262 (Asp residue) is substituted with Gly, Ser, Thr, Cys or Val residue, the amino acid residue at position 149 (Lys residue) is substituted with Asn residue, or the amino acid residue at position 198 (Lys residue) is substituted with Glu residue; and a protein having an amino acid sequence with at least 80% identity to the amino acid sequence represented by SEQ ID NO: 2 wherein the amino acid residue corresponding to position 48 of amino acid sequence represented by SEQ ID NO: 2 is substituted with Ala, Gly, Thr, Arg, Glu, Asn or Gln residue, the amino acid residue corresponding to position 262 is substituted with Gly, Ser, Thr, Cys or Val residue, the amino acid residue corresponding to position 149 is substituted with Asn residue, or the amino acid residue corresponding to position 198 is substituted with Glu residue.

In addition, a single or a multiple amino acid substitution can be made regarding (a) position 48, (b) position 262, (c) position 149 and (d) position 198.

Herein, with respect to the method for identifying an "amino acid residue corresponding to (a certain) position", comparison of an amino acid sequence is made with a known algorithm such as Lipman-Pearson method, and then by giving the highest homology to a conserved amino acid residue present in the amino acid sequence of each plasmid replication protein the identification can be carried out. In addition, with alignment of the amino acid sequence contained in a plasmid replication protein according to the method, position of the each amino acid residue having homology can be determined against the sequence of each plasmid replication protein, regardless of an insertion or deletion contained in the amino acid sequence. A homology position is believed to be present at the same position in a three-dimensional structure, and presumably has a similar effect regarding a specific function of a plasmid replication protein.

The plasmid vector of the present invention can be constructed by introducing a mutation to DNA encoding a plasmid replication protein based on a site specific mutagenesis that is generally used. More specifically, it can be carried out by using Site-Directed Mutagenesis System Mutan-Super Express Km Kit (Takara Bio Inc.) and the like, for example. Further, by employing recombinant PCR (polymerase chain reaction; PCR protocols, Academic Press, New York, 1990), any sequence in a gene can be replaced with a sequence in other gene which corresponds to the any sequence.

With ligation of a DNA fragment which includes a DNA replication initiation region, an antibiotics-resistant gene, a DNA region including a replication origin, a promoter region for initiating transcription and a secretory signal region, and a gene which encodes a target product of a heterologous gene to the DNA which encodes the plasmid replication protein of the present invention, a recombinant plasmid which can be used for large-scale production of a target gene product such as a protein, a polypeptide, and the like can be constructed.

The "heterologous gene" includes a gene encoding an enzyme such as amylase, protease, cellulase, lipase, pectinase, pllulanase, peroxidase, oxygenase, catalase and the like, and a gene encoding a physiologically active peptide such as insulin, human growth hormone, interferon, calcitonin, interleukin and the like, but is not specifically limited thereto.

The "promoter region for initiating transcription and a secretory signal region" means a nucleotide sequence of a regulatory region which is related to transcription, translation and secretion of a heterologous gene. Examples of "the promoter region for initiating transcription" include, a transcription initiation regulatory region including a promoter and a transcription origin, a ribosome binding site, a translation initiation region including an initiation codon, and combination thereof. Examples of "the secretory signal region" include a secretory signal peptide region.

In the plasmid vector of the present invention, a target heterologous gene, and a regulatory region relating to transcription, translation and secretion are operatively linked to each other (for example, a regulatory region is placed at upstream region of a heterologous gene). The regulatory region preferably contains three regions including a transcription initiation regulatory region, a translation initiation regulatory region, and a secretory signal region. More preferably, the secretory signal region is from cellulase gene of a microorganism, Bacillus spp., and the transcription initiation region and the translation initiation region are 0.6 to 1 kb upstream of the corresponding cellulase gene. More preferably, the regulatory region is the transcription initiation regulatory region, the translation initiation region and the secretory signal peptide region from cellulase gene of strain KSM-S237 (FERM BP-7875) or strain KSM-64 (FERM BP-2886), both belonging to Bacillus spp. Even more preferably, the regulatory region is a nucleotide sequence of base numbers 1 to 659 of the nucleotide sequence represented by SEQ ID NO: 13, a nucleotide sequence of base numbers 1 to 696 of the gene encoding cellulase with the nucleotide sequence represented by SEQ ID NO: 14, a nucleotide sequence having at least 70%, preferably at least 80%, more preferably at least 90%, more preferably at least 95%, and even more preferably at least 98% identity to the corresponding nucleotide sequence, or a nucleotide sequence wherein part of any nucleotide sequence described above is deleted. With respect to the nucleotide sequence wherein part of any nucleotide sequence described above is deleted, it indicates a sequence lacking part of the above described nucleotide sequence but still maintaining a function related to transcription, translation, and secretion of a gene.

Herein below, one example for constructing the plasmid vector of the present invention for producing KP43 protease from Bacillus sp. strain KSM-KP43 is described (see FIG. 1).

KP43 protease gene from Bacillus sp. strain KSM-KP43 is ligated to a downstream region of the promoter region and the secretory signal region of cellulase gene of Bacillus sp. strain KSM-64 (FERN BP-2886). In addition, pAMα1 as a replication region and tetracycline resistant gene as an antibiotics-resistant gene are ligated thereto. In the thus constructed recombinant plasmid vector, primers in both forward and reverse directions are prepared so as to have a restriction enzyme site (Xba I) that is present downstream of the KP43 gene (i.e., primers a and d in FIG. 1) located between them. In addition, other primers in both forward and reverse directions are prepared so as to have a new restriction enzyme site (Nhe I) downstream of the Ori-pAMα1 gene (i.e., primers b and c in FIG. 1). Two fragments that are obtained by PCR (i.e., a region including Tc and KP43, and a region including pAMα1) are placed so as to have them ligated after the digestion by Xba I and Nhe I. In FIG. 1, with respect to the region including pAMα1 that is amplified by primers b and d, by promoting the occurrence of an error during amplification process, a plasmid vector having a random mutation in a replicated protein region can be constructed.

By transforming a host microorganism with the plasmid vector as obtained above, a recombinant microorganism of the present invention can be produced. Further, by culturing this recombinant microorganism and collecting a target protein or polypeptide from the culture, the target protein or the polypeptide can be produced in large scale. With respect to a host microorganism for transformation, microorganisms of Staphylococcus spp., Enterococcus spp., Listeria spp., Bacillus spp. and the like can be mentioned. Among these, Bacillus spp. is preferred.

Types of a culture medium used for culturing the recombinant microorganism are not specifically limited as long as the recombinant microorganism can grow and an enzyme can be produced therefrom. In addition, for a culture medium, a nitrogen source and a carbon source are combined in an appropriate concentration, and inorganic salts, metal salts and the like with an appropriate concentration are added. pH and temperature of a culture medium is not specifically limited as long as the recombinant microorganism can grow therein.

Further, isolation of a target protein or polypeptide produced can be carried out according to an ordinary method, and if necessary, purification, crystallization and granulation can be also performed.

EXAMPLES

Example 1

Effect of Mutation at Rep48 Position

Based on productivity of the mutant protease having an improved secretion property or specific activity of alkaline protease from Bacillus sp. strain KSM-KP43 as described in JP-A-2002-218989, JP-A-2002-306176, or JP-A-2004-122 (alkaline protease having nucleotide sequence of SEQ ID NO: 3 or SEQ ID NO: 4 wherein Phe at position 46 is substituted with Leu, Thr at position 65 is substituted with Pro, Tyr at position 195 is substituted with His, Val at position 273 is substituted with Ile, Thr at position 359 is substituted with Ser, Asp at position 369 is substituted with Asn, and Ser at position 387 is substituted with Ala; herein below referred to as 'KP43H2'), effect of mutation at Rep48 position was determined.

Mutation on Rep was introduced by performing PCR in Takara Thermal Cycler Type 480 using pHA64-KP43H2 as a template. pHA64-KP43H2 is a plasmid vector in which the structural gene of KP43H2 and a terminator are ligated to the BamH I and Xba I sites of the expression vector pHA64 which is a plasmid vector including the replication origin of plasmid pAMα1 or pUB110, the replication protein (Rep) and an antibiotics-resistant gene (JP-A-03-259086), and also has the promoter region and the secretory signal region of alkaline cellulase K-64 of *Bacillus* sp. strain KSM-64 (JP-A-2000-287687). Specifically, to 0.1 to 0.5 ng of the circular plasmid as a template, 20 pmol each of primer pair for introducing a mutation (i.e., SEQ ID NO: 5 and SEQ ID NO: 9 or SEQ ID NO: 7 and SEQ ID NO: 10), 20 nmol each of dNTPs, 5 µL of buffer for Takara Pyrobest DNA polymerase, and 2 U of Pyrobest DNA polymerase were added to prepare a reaction solution (50 µL). As a PCR condition, after denaturing at 94° C. for one minute, a cycle of one minute at 94° C., one minute at 55° C., four minutes at 72° C. was repeated thirty times (i.e., 30 cycles), and as a last reaction the mixture was incubated for 10 minutes at 72° C.

Thus obtained PCR products were purified with High Pure PCR Product Purification kit (Roche), eluted with 100 µL of sterilized water, and then amplified as a single fragment with the primers (SEQ ID NO: 5 and SEQ ID NO: 7), each of which locates at each end of the single fragment. Specifically, each of the two fragments that had been obtained from the first PCR was 100-fold diluted, mixed and then subjected to PCR with the condition same as the above described. The amplified DNA fragment was identified with electrophoresis, digested with Nhe I and Xba I, and then by using DNA Ligation kit ver.2 (Takara Bio Inc.), ligated to a fragment obtained from digestion with Nhe I and Xba I of the fragment that had been amplified with primers of SEQ ID NO: 6 and SEQ ID NO: 8 according to the above described method by having pHA64-KP43H2 as a template wherein tetracycline resistant gene and KP43H2 gene were included.

The reaction solution was purified with High Pure PCR Product Purification kit (Roche), and then eluted with 100 µL sterilized water. The resulting DNA solution was used for transformation of *Bacillus* sp. strain KSM-KP43 based on an electroporation method using Gene Pulser cuvette (Biorad). Transformed cells were cultured on an alkaline agar medium including skim milk [Skim milk (Difco) 1% (w/v), Bacto Tryptone (Difco) 1%, yeast extract (Difco) 0.5%, sodium chloride 0.5%, agar 1.5%, anhydrous sodium carbonate 0.05%, tetracycline 15 ppm] and then the presence or the absence of protease gene in the cells was determined in view of the formation of lysis mark of skim milk. A transformant which contains the plasmid having the protease gene inserted in pHA64 was selected and then used for further culture.

For each transformant, single colony formation and halo formation were confirmed. After that, the transformant was inoculated in 5 mL starter culture medium in a test tube [Polypeptone S (Nihon Seiyaku) 6.0% (w/v), yeast extract 0.1%, maltose 1.0%, magnesium sulfate heptahydrate 0.02%, potassium dihydrophosphate 0.1%, anhydrous sodium carbonate 0.3%, tetracycline 30 ppm], and cultured overnight at 30° C., 320 rpm. The resulting starting culture solution was inoculated (1% (v/v)) to 20 mL main medium [Polypeptone S 8% (w/v), yeast extract 0.3%, maltose 10%, magnesium sulfate heptahydrate 0.04%, potassium dihydrophosphate 0.2%, anhydrous sodium carbonate 1.5%, tetracycline 30 ppm] contained in a 500 mL Sakaguchi flask, and cultured for three days at 30° C., 121 rpm. The resulting culture was centrifuged and the supernatant was taken for determination of a protease activity. Protease activity was determined according to casein method. Protein concentration was determined by using a protein assay kit (Wako Pure Chemicals). As a result, it was found that the activity of alkaline protease KP43H2 that had been produced by using the plasmid having a mutated Rep gene was improved in an amount of 8 to 12% compared to the control (pHA64-KP43H2 transformant cultured under the same condition) (see, Table 1). In addition, the amount of protein in the culture supernatant increases almost in proportion to the activity of protease, indicating that the resulting mutant contains the mutation that is required for enhanced secretion of a protein. Further, the plasmid was extracted from the selected transformant to determine its nucleotide sequence by sequencing. As a result, it was confirmed that the resulting plasmid corresponds to the desired mutant.

TABLE 1

| Rep48 position | KP43H2 activity |
|---|---|
| Lys(wild) | 100 |
| Ala | 112 |
| Gly | 111 |
| Thr | 109 |
| Arg | 109 |
| Glu | 111 |
| Asn | 108 |
| Gln | 110 |

The alkaline protease that had been obtained by the above described mutation still maintains characteristics of the parent alkaline protease such as resistance to an oxidizing agent and resistance to inhibition of casein degradation activity by high concentration fatty acids, molecular weight of 43,000±2,000 recognized by SDS-PAGE, and an activity in an alkaline condition, except that the enzyme secretion is promoted in a transformant.

Example 2

Effect of Mutation at Rep262 Position

In a similar manner to Example 1, based on productivity of the mutant alkaline protease from *Bacillus* sp. strain KSM-KP43, mutation effect at Rep262 position was determined.

Specifically, PCR was performed with a primer pair for introducing a mutation (i.e., SEQ ID NO: 5 and SEQ ID NO: 11 or SEQ ID NO: 7 and SEQ ID NO: 12) using 0.1 to 0.5 ng of pHA64-KP43H2 as a template, to thereby obtain two fragments amplified in a similar manner to Example 1. Then, the two fragments were amplified as a single fragment with the primers (i.e., SEQ ID NO: 5 and SEQ ID NO: 7), each of which locates at each end of the single fragment. Thus obtained DNA fragment was identified with electrophoresis, digested with Nhe I and Xba I, and then by using DNA Ligation kit ver.2 (Takara Bio Inc.) the DNA fragment was ligated to a fragment obtained from digestion with Nhe I and Xba I of the fragment that had been amplified with primers of SEQ ID NO: 6 and SEQ ID NO: 8 according to the above described method by using pHA64-KP43H2 as a template wherein tetracycline resistant gene and KP43H2 gene were included. Subsequently, transformation was carried out.

The presence or the absence of protease gene in the cells was determined in view of the formation of lysis mark of skim milk that was produced from the transformant cultured on alkaline agar medium including skim milk (Example 1). A transformant which contains the plasmid having the protease gene inserted in pHA64 was selected and then used for further culture in a similar manner to Example 1.

As a result, it was found that the activity of alkaline protease KP43H2, that had been produced by using the plasmid having a mutated Rep gene, was improved in an amount of 3 to 13% compared to the control (pHA64-KP43H2 transformant cultured under the same condition) (see, Table 2). In addition, from the result that the amount of protein in the culture supernatant increases almost in proportion to the activity of protease, it can be said that the resulting mutant contains the mutation that is required for enhanced secretion of a protein. Further, the plasmid was extracted from the selected transformant and its nucleotide sequence was determined by sequencing. As a result, it was confirmed that the resulting plasmid corresponds to the desired mutant.

TABLE 2

| Rep262 position | KP43H2 Activity |
| --- | --- |
| Asp(wild) | 100 |
| Gly | 103 |
| Ser | 109 |
| Thr | 107 |
| Cys | 113 |
| Val | 109 |

Example 3

Effect of Random Mutation on Rep

Based on productivity of the mutant protease having an improved secretion property or specific activity of alkaline protease from *Bacillus* sp. strain KSM-KP43 as described in JP-A-2002-218989, JP-A-2002-306176, JP-A-2004-122 or JP-A-2004-305176 (alkaline protease having nucleotide sequence of SEQ ID NO: 3 or SEQ ID NO: 4 wherein Ser at position 15 is substituted with His, Ser at position 16 is substituted with Gln, Phe at position 46 is substituted with Leu, Thr at position 65 is substituted with Pro, Asn at position 166 is substituted with Gly, Gly at position 167 is substituted with Val, Asn at position 187 is substituted with Ser, Tyr at position 195 is substituted with Gln, Val at position 273 is substituted with Ile, Lys at position 346 is substituted with Arg, Thr at position 359 is substituted with Ser, Asp at position 369 is substituted with Asn, Ser at position 387 is substituted with Ala, and Asn at position 405 is substituted with Asp; herein below, referred to as 'KP43H3'), effect of mutation at Rep48 position was determined.

With a pHA64-KP43H3 as a template in which KP43H3 had been introduced to BamH I and Xba I sites of pHA64, random mutation was introduced on Rep by PCR in Takara Thermal Cycler Type 480. Specifically, to 0.1 to 0.5 ng of the circular plasmid as a template, 20 pmol each of primer pair (i.e., SEQ ID NO: 5 and SEQ ID NO: 7), 20 nmol each of dNTPs, 5 μL of buffer for Takara Pyrobest DNA polymerase, 2 U of Pyrobest DNA polymerase, 7.5% DMSO and 0.05-0.1 mM manganese sulfate were added to prepare a reaction solution (50 μL). As a PCR condition, after denaturing at 94° C. for one minute, a cycle of one minute at 94° C., one minute at 55° C., four minutes at 72° C. was repeated thirty times (i.e., 30 cycles), and as a last reaction the mixture was incubated for 10 minutes at 72° C.

Thus obtained PCR product was purified with High Pure PCR Product Purification kit (Roche), eluted with 100 μL of sterilized water, and then the resulting amplified DNA fragment was identified by electrophoresis. After digestion with Nhe I and Xba I, by using DNA Ligation kit ver.2 (Takara Bio Inc.) the DNA fragment was ligated to the fragment obtained from digesion with Nhe I and Xba I of the fragment that had been amplified with primers of SEQ ID NO: 6 and SEQ ID NO: 8 according to the above described method by using pHA64-KP43H3 as a template wherein tetracycline resistant gene and KP43H2 gene are included.

The transformation was carried out in a similar manner to Example 1. Then, the presence or the absence of protease gene in the cells was determined in view of the formation of lysis mark of skim milk that was produced from the transformant cultured on alkaline agar medium including skim milk. A transformant which contains the plasmid having the protease gene inserted in pHA64 was selected and then used for further culture.

As a result, it was found that, among the alkaline protease KP43H3 that had been produced by using the plasmid having a mutated Rep gene, Lys149Asn and Lys198Glu have the activity that is improved in an amount of 7% compared to the control (pHA64-KP43H3 transformant cultured under the same condition) (see, Table 3). In addition, from the result that the amount of protein in the culture supernatant increases almost in proportion to the activity of protease, indicating that the resulting mutant contains the mutation that is required for enhanced secretion of a protein. Further, the plasmid was extracted from the selected transformant and its nucleotide sequence was determined by sequencing. Consequently, it was confirmed that the resulting plasmid corresponds to the desired mutant.

TABLE 3

| Rep mutation position | KP43H3 activity |
| --- | --- |
| wild | 100 |
| Lys149Asn | 107 |
| Lys198Glu | 107 |

What is claimed is:

1. A plasmid vector comprising DNA which encodes a plasmid replication protein, wherein the amino acid sequence of said replication protein comprises the sequence of SEQ ID NO:2 except that, as compared to SEQ ID NO:2, the amino acid sequence of said replication protein comprises one or more substitutions selected from the group consisting of
   (a) Ala, Gly, Thr, Arg, Glu, Asn, or Gln at SEQ ID NO:2 amino acid residue position 48,
   (b) Gly, Ser, Thr, Cys or Val at SEQ ID NO:2 amino acid residue position 262,
   (c) Asn at SEQ ID NO:2 amino acid residue position 149, and
   (d) Glu at SEQ ID NO:2 amino acid residue position 198.

2. A plasmid vector comprising DNA which encodes a plasmid replication protein, wherein the replication protein comprises a sequence that has at least 90% identity a to the sequence of SEQ ID NO:2 except that, as compared to SEQ ID NO:2, the amino acid sequence of said replication protein comprises one or more substitutions selected from the group consisting of
   (a) Ala, Gly, Thr, Arm Glu, Asn or Gln at the position corresponding to SEQ ID NO:2 amino acid residue position 48,
   (b) Gly, Ser, Thr, Cys or Val, at the position corresponding to SEQ ID NO:2 amino acid residue position 262,
   (c) Asn at the position corresponding to SEQ ID NO:2 amino acid residue position 149, and
   (d) Glu at the position corresponding, to SEQ ID NO:2 amino acid residue position 198.

3. The plasmid vector according to claim 1 or 2, further comprising a nucleotide sequence of a promoter region and a secretory signal region of a *Bacillus* spp, alkaline cellulase gene.

4. The plasmid vector according to claim 3, wherein the nucleotide sequence of said promoter region and secretory signal region of a said *Bacillus* spp alkaline cellulase gene is:
   (i) a polynucleotide sequence comprising nucleotides 1 to 659 of cellulase gene which consists of a nucleotide sequence of SEQ ID NO: 13,
   (ii) a polynucleotide sequence comprising nucleotides 1 to 696 of cellulase gene which consists of a nucleotide sequence of SEQ ID NO: 14, or
   (iii) a polynucleotide sequence having at least 95% identity to the nucleotide sequence of (i) or (ii).

5. An isolated transformed host cell, transformed with the plasmid vector of claim 3.

6. The isolated transformed host cell according to claim 5, wherein said host cell is a *Bacillus*.

7. A method for producing a polypeptide comprising the steps of:
   constructing a plasmid vector comprising DNA which encodes a target polypeptide and DNA which encodes a plasmid replication protein, wherein the amino acid sequence of said replication protein comprises the sequence of SEQ ID NO:2 except that, as compared to SEQ ID NO:2, the amino acid sequence of said replication protein comprises one or more substitutions selected from the group consisting of
   (a) Ala, Gly, Thr, Asn or Glu, Asn or Gln at SEQ NO:2 position 48,
   (b) Gly, Ser, Thr, Cys or Val at SEQ ID NO:2 position 262,
   (c) Asn at SEQ ID NO:2 position 149, and
   (d) Glu at SEQ ID NO:2 position 198
   transforming a host microorganism with the plasmid vector; and culturing the host microorganism and collecting the target polypeptide produced therefrom.

8. A method for producing a polypeptide comprising the steps of:
   constructing a plasmid vector comprising DNA which encodes a target polypeptide and DNA which encodes a plasmid replication protein, wherein the replication protein comprises a sequence that has at least 90% identity to the sequence of SEQ ID NO:2 except, that, as compared to SEQ ID NO:2, the amino acid sequence said replication protein comprises one or more substitutions selected from the group consisting of
   (a) Ala, Gly, Thr, Arg, Glu, Asn or Gln at the position corresponding to SEQ ID NO:2 amino acid residue position 48,
   (b) Gly, Ser, Thr, Cys or Val at the position corresponding to SEQ ID NO:2 amino acid residue position 262,
   (c) Asn at the position corresponding, to SEQ ID NO:2 amino acid residue position 149, and
   (d) Glu at the position corresponding to SEQ ID NO:2 amino acid residue position 198;
   transforming a host microorganism with the plasmid vector; and culturing the host microorganism and collecting the target polypeptide produced therefrom.

9. The method according to claim 7 or 8, wherein the plasmid vector further comprises a nucleotide sequence of a promoter region and a secretory signal region of a *Bacillus* spp. alkaline cellulase gene.

10. The method according to claim 9, wherein the nucleotide sequences of said promoter region and secretory signal region of said *Bacillus* spp. alkaline cellulase gene is:
    (i) a polynucleotide nucleotide sequence comprising nucleotides 1 to 659 of a cellulase gene which consists of the nucleotide sequence of SEQ ID NO: 13,
    (ii) a polynucleotide nucleotide sequence comprising nucleotides 1 to 696 of a cellulase gene which consists of the nucleotide sequence of SEQ ID NO: 14, or
    (iii) a polynucleotide sequence having at least 95% identity to the nucleotide sequence of (i) or (ii).

11. An isolated transformed host cell comprising the plasmid vector according to claim 4.

12. The isolated transformed host cell according to claim 11, wherein said transformant is a *Bacillus*.

* * * * *

UNITED STATES PATENT AND TRADEMARK OFFICE
CERTIFICATE OF CORRECTION

PATENT NO. : 8,389,685 B2
APPLICATION NO. : 12/934395
DATED : March 5, 2013
INVENTOR(S) : Takimura et al.

Page 1 of 1

It is certified that error appears in the above-identified patent and that said Letters Patent is hereby corrected as shown below:

In the Claims:

Column 37
Line 32, please replace "(a) Ala, ... , Thr, Arm, ..." with --(a) Ala, ... , Thr, Arg, ...--.

Column 38
Line 15, please replace "(a) Ala, ... , Thr, Asn, ..." with --(a) Ala, ... , Thr, Arg, ...--.

Signed and Sealed this
Twenty-first Day of May, 2013

Teresa Stanek Rea
*Acting Director of the United States Patent and Trademark Office*

SEQUENCE LISTING

<160> NUMBER OF SEQ ID NOS: 14

<210> SEQ ID NO 1
<211> LENGTH: 984
<212> TYPE: DNA

```
<213> ORGANISM: Enterococus faecalis
<220> FEATURE:
<221> NAME/KEY: CDS
<222> LOCATION: (1)..(984)

<400> SEQUENCE: 1 atg tgt cct aat agt agc att tat tca gat gaa aaa tca agg gtt tta      48
Met Cys Pro Asn Ser Ser Ile Tyr Ser Asp Glu Lys Ser Arg Val Leu
1               5                   10                  15 gtg gac aag aca aaa agt gga aaa gtg aga cca tgg aga gaa aag aaa      96
Val Asp Lys Thr Lys Ser Gly Lys Val Arg Pro Trp Arg Glu Lys Lys
            20                  25                  30 atc gct aat gtt gat tac ttt gaa ctt ctg cat att ctt gaa ttt aaa     144
Ile Ala Asn Val Asp Tyr Phe Glu Leu Leu His Ile Leu Glu Phe Lys
        35                  40                  45 aag gct gaa aga gta aaa gat tgt gct gaa ata tta gag tat aaa caa     192
Lys Ala Glu Arg Val Lys Asp Cys Ala Glu Ile Leu Glu Tyr Lys Gln
    50                  55                  60 aat cgt gaa aca ggc gaa aga aag ttg tat cga gtg tgg ttt tgt aaa     240
Asn Arg Glu Thr Gly Glu Arg Lys Leu Tyr Arg Val Trp Phe Cys Lys
65                  70                  75                  80 tcc agg ctt tgt cca atg tgc aac tgg agg aga gca atg aaa cat ggc     288
Ser Arg Leu Cys Pro Met Cys Asn Trp Arg Arg Ala Met Lys His Gly
                85                  90                  95 att cag tca caa aag gtt gtt gct gaa gtt att aaa caa aag cca aca     336
Ile Gln Ser Gln Lys Val Val Ala Glu Val Ile Lys Gln Lys Pro Thr
            100                 105                 110 gtt cgt tgg ttg ttt ctc aca tta aca gtt aaa aat gtt tat gat ggc     384
Val Arg Trp Leu Phe Leu Thr Leu Thr Val Lys Asn Val Tyr Asp Gly
        115                 120                 125 gaa gaa tta aat aag agt ttg tca gat atg gct caa gga ttt cgc cga     432
Glu Glu Leu Asn Lys Ser Leu Ser Asp Met Ala Gln Gly Phe Arg Arg
    130                 135                 140 atg atg caa tat aaa aaa att aat aaa aat ctt gtt ggt ttt atg cgt     480
Met Met Gln Tyr Lys Lys Ile Asn Lys Asn Leu Val Gly Phe Met Arg
145                 150                 155                 160 gca acg gaa gtg aca ata aat aat aaa gat aat tct tat aat cag cac     528
Ala Thr Glu Val Thr Ile Asn Asn Lys Asp Asn Ser Tyr Asn Gln His
                165                 170                 175 atg cat gta ttg gta tgt gtg gaa cca act tat ttt aag aat aca gaa     576
Met His Val Leu Val Cys Val Glu Pro Thr Tyr Phe Lys Asn Thr Glu
            180                 185                 190 aac tac gtg aat caa aaa caa tgg att caa ttt tgg aaa aag gca atg     624
Asn Tyr Val Asn Gln Lys Gln Trp Ile Gln Phe Trp Lys Lys Ala Met
        195                 200                 205 aaa tta gac tat gat cca aat gta aaa gtt caa atg att cga ccg aaa     672
Lys Leu Asp Tyr Asp Pro Asn Val Lys Val Gln Met Ile Arg Pro Lys
    210                 215                 220 aat aaa tat aaa tcg gat ata caa tcg gca att gac gaa act gca aaa     720
Asn Lys Tyr Lys Ser Asp Ile Gln Ser Ala Ile Asp Glu Thr Ala Lys
225                 230                 235                 240 tat cct gta aag gat acg gat ttt atg acc gat gat gaa gaa aag aat     768
Tyr Pro Val Lys Asp Thr Asp Phe Met Thr Asp Asp Glu Glu Lys Asn
                245                 250                 255 ttg aaa cgt ttg tct gat ttg gag gaa ggt tta cac cgt aaa agg tta     816
Leu Lys Arg Leu Ser Asp Leu Glu Glu Gly Leu His Arg Lys Arg Leu
            260                 265                 270 atc tcc tat ggt ggt ttg tta aaa gaa ata cat aaa aaa tta aac ctt     864
Ile Ser Tyr Gly Gly Leu Leu Lys Glu Ile His Lys Lys Leu Asn Leu
        275                 280                 285 gat gac aca gaa gaa ggc gat ttg att cat aca gat gat gac gaa aaa     912
Asp Asp Thr Glu Glu Gly Asp Leu Ile His Thr Asp Asp Asp Glu Lys
```

```
Asp Asp Thr Glu Glu Gly Asp Leu Ile His Thr Asp Asp Glu Lys
        290                 295                 300 gcc gat gaa gat gga ttt tct att att gca atg tgg aat tgg gaa cgg      960
Ala Asp Glu Asp Gly Phe Ser Ile Ile Ala Met Trp Asn Trp Glu Arg
305                 310                 315                 320 aaa aat tat ttt att aaa gag tag                                      984
Lys Asn Tyr Phe Ile Lys Glu
                325

<210> SEQ ID NO 2
<211> LENGTH: 327
<212> TYPE: PRT
<213> ORGANISM: Enterococus faecalis

<400> SEQUENCE: 2

Met Cys Pro Asn Ser Ser Ile Tyr Ser Asp Glu Lys Ser Arg Val Leu
1               5                   10                  15

Val Asp Lys Thr Lys Ser Gly Lys Val Arg Pro Trp Arg Glu Lys Lys
            20                  25                  30

Ile Ala Asn Val Asp Tyr Phe Glu Leu Leu His Ile Leu Glu Phe Lys
        35                  40                  45

Lys Ala Glu Arg Val Lys Asp Cys Ala Glu Ile Leu Glu Tyr Lys Gln
    50                  55                  60

Asn Arg Glu Thr Gly Glu Arg Lys Leu Tyr Arg Val Trp Phe Cys Lys
65                  70                  75                  80

Ser Arg Leu Cys Pro Met Cys Asn Trp Arg Arg Ala Met Lys His Gly
                85                  90                  95

Ile Gln Ser Gln Lys Val Val Ala Glu Val Ile Lys Gln Lys Pro Thr
            100                 105                 110

Val Arg Trp Leu Phe Leu Thr Leu Thr Val Lys Asn Val Tyr Asp Gly
        115                 120                 125

Glu Glu Leu Asn Lys Ser Leu Ser Asp Met Ala Gln Gly Phe Arg Arg
    130                 135                 140

Met Met Gln Tyr Lys Lys Ile Asn Lys Asn Leu Val Gly Phe Met Arg
145                 150                 155                 160

Ala Thr Glu Val Thr Ile Asn Asn Lys Asp Asn Ser Tyr Asn Gln His
                165                 170                 175

Met His Val Leu Val Cys Val Glu Pro Thr Tyr Phe Lys Asn Thr Glu
            180                 185                 190

Asn Tyr Val Asn Gln Lys Gln Trp Ile Gln Phe Trp Lys Lys Ala Met
        195                 200                 205

Lys Leu Asp Tyr Asp Pro Asn Val Lys Val Gln Met Ile Arg Pro Lys
    210                 215                 220

Asn Lys Tyr Lys Ser Asp Ile Gln Ser Ala Ile Asp Glu Thr Ala Lys
225                 230                 235                 240

Tyr Pro Val Lys Asp Thr Asp Phe Met Thr Asp Asp Glu Lys Asn
                245                 250                 255

Leu Lys Arg Leu Ser Asp Leu Glu Glu Gly Leu His Arg Lys Arg Leu
        260                 265                 270

Ile Ser Tyr Gly Gly Leu Leu Lys Glu Ile His Lys Lys Leu Asn Leu
    275                 280                 285

Asp Asp Thr Glu Glu Gly Asp Leu Ile His Thr Asp Asp Glu Lys
        290                 295                 300

Ala Asp Glu Asp Gly Phe Ser Ile Ile Ala Met Trp Asn Trp Glu Arg
305                 310                 315                 320

Lys Asn Tyr Phe Ile Lys Glu
```

```
<210> SEQ ID NO 3
<211> LENGTH: 1923
<212> TYPE: DNA
<213> ORGANISM: Bacillus sp. KSM-KP43
<220> FEATURE:
<221> NAME/KEY: CDS
<222> LOCATION: (1)..(1920)
<220> FEATURE:
<221> NAME/KEY: sig_peptide
<222> LOCATION: (1)..(618)
<220> FEATURE:
<221> NAME/KEY: mat_peptide
<222> LOCATION: (619)..(1920)

<400> SEQUENCE: 3
```

| | | | | | | | | | | | | | | | |
|---|---|---|---|---|---|---|---|---|---|---|---|---|---|---|---|
| atg | aga | aag | aag | aaa | aag | gtg | ttt | tta | tct | gtt | tta | tca | gct | gca | 45 |
| Met | Arg | Lys | Lys | Lys | Lys | Val | Phe | Leu | Ser | Val | Leu | Ser | Ala | Ala | |
| | -205 | | | | -200 | | | | | -195 | | | | | |
| gcg | att | ttg | tcg | act | gtt | gcg | tta | agt | aat | cca | tct | gca | ggt | ggt | 90 |
| Ala | Ile | Leu | Ser | Thr | Val | Ala | Leu | Ser | Asn | Pro | Ser | Ala | Gly | Gly | |
| | -190 | | | | -185 | | | | | -180 | | | | | |
| gca | agg | aat | ttt | gat | ctg | gat | ttc | aaa | gga | att | cag | aca | aca | act | 135 |
| Ala | Arg | Asn | Phe | Asp | Leu | Asp | Phe | Lys | Gly | Ile | Gln | Thr | Thr | Thr | |
| | -175 | | | | -170 | | | | | -165 | | | | | |
| gat | gct | aaa | ggt | ttc | tcc | aag | cag | ggg | cag | act | ggt | gct | gct | gct | 180 |
| Asp | Ala | Lys | Gly | Phe | Ser | Lys | Gln | Gly | Gln | Thr | Gly | Ala | Ala | Ala | |
| | -160 | | | | -155 | | | | | -150 | | | | | |
| ttt | ctg | gtg | gaa | tct | gaa | aat | gtg | aaa | ctc | cca | aaa | ggt | ttg | cag | 225 |
| Phe | Leu | Val | Glu | Ser | Glu | Asn | Val | Lys | Leu | Pro | Lys | Gly | Leu | Gln | |
| | -145 | | | | -140 | | | | | -135 | | | | | |
| aag | aag | ctt | gaa | aca | gtc | ccg | gca | aat | aat | aaa | ctc | cat | att | atc | 270 |
| Lys | Lys | Leu | Glu | Thr | Val | Pro | Ala | Asn | Asn | Lys | Leu | His | Ile | Ile | |
| | -130 | | | | -125 | | | | | -120 | | | | | |
| caa | ttc | aat | gga | cca | att | tta | gaa | gaa | aca | aaa | cag | cag | ctg | gaa | 315 |
| Gln | Phe | Asn | Gly | Pro | Ile | Leu | Glu | Glu | Thr | Lys | Gln | Gln | Leu | Glu | |
| | -115 | | | | -110 | | | | | -105 | | | | | |
| aaa | aca | ggg | gca | aag | att | ctc | gac | tac | ata | cct | gat | tat | gct | tac | att | 363 |
| Lys | Thr | Gly | Ala | Lys | Ile | Leu | Asp | Tyr | Ile | Pro | Asp | Tyr | Ala | Tyr | Ile |
| | -100 | | | | -95 | | | | | -90 | | | | | |
| gtc | gag | tat | gag | ggc | gat | gtt | aag | tca | gca | aca | agc | acc | att | gag | cac | 411 |
| Val | Glu | Tyr | Glu | Gly | Asp | Val | Lys | Ser | Ala | Thr | Ser | Thr | Ile | Glu | His |
| -85 | | | | -80 | | | | | -75 | | | | | -70 | |
| gtg | gaa | tcc | gtg | gag | cct | tat | ttg | ccg | ata | tac | aga | ata | gat | ccc | cag | 459 |
| Val | Glu | Ser | Val | Glu | Pro | Tyr | Leu | Pro | Ile | Tyr | Arg | Ile | Asp | Pro | Gln |
| | | | -65 | | | | | -60 | | | | | -55 | | |
| ctt | ttc | aca | aaa | ggg | gca | tca | gag | ctt | gta | aaa | gca | gtg | gcg | ctt | gat | 507 |
| Leu | Phe | Thr | Lys | Gly | Ala | Ser | Glu | Leu | Val | Lys | Ala | Val | Ala | Leu | Asp |
| | | | -50 | | | | | -45 | | | | | -40 | | |
| aca | aag | cag | aaa | aat | aaa | gag | gtg | caa | tta | aga | ggc | atc | gaa | caa | atc | 555 |
| Thr | Lys | Gln | Lys | Asn | Lys | Glu | Val | Gln | Leu | Arg | Gly | Ile | Glu | Gln | Ile |
| | | | -35 | | | | | -30 | | | | | -25 | | |
| gca | caa | ttc | gca | ata | agc | aat | gat | gtg | cta | tat | att | acg | gca | aag | cct | 603 |
| Ala | Gln | Phe | Ala | Ile | Ser | Asn | Asp | Val | Leu | Tyr | Ile | Thr | Ala | Lys | Pro |
| | | | -20 | | | | | -15 | | | | | -10 | | |
| gag | tat | aag | gtg | atg | aat | gat | gtt | gcg | cgt | gga | att | gtc | aaa | gcg | gat | 651 |
| Glu | Tyr | Lys | Val | Met | Asn | Asp | Val | Ala | Arg | Gly | Ile | Val | Lys | Ala | Asp |
| -5 | | | | -1 | 1 | | | | 5 | | | | | 10 | |
| gtg | gct | cag | agc | agc | tac | ggg | ttg | tat | gga | caa | gga | cag | atc | gta | gcg | 699 |
| Val | Ala | Gln | Ser | Ser | Tyr | Gly | Leu | Tyr | Gly | Gln | Gly | Gln | Ile | Val | Ala |
| | | | 15 | | | | | 20 | | | | | 25 | | |
| gtt | gcc | gat | aca | ggg | ctt | gat | aca | ggt | cgc | aat | gac | agt | tcg | atg | cat | 747 |

```
                Val Ala Asp Thr Gly Leu Asp Thr Gly Arg Asn Asp Ser Ser Met His
                        30                  35                  40 gaa gcc ttc cgc ggg aaa att acc gca tta tat gca ttg gga cgg acg              795
Glu Ala Phe Arg Gly Lys Ile Thr Ala Leu Tyr Ala Leu Gly Arg Thr
 45                  50                  55 aat aat gcc aat gat acg aat ggt cat ggt acg cat gtg gct ggc tcc              843
Asn Asn Ala Asn Asp Thr Asn Gly His Gly Thr His Val Ala Gly Ser
 60                  65                  70                  75 gta tta gga aac ggc tcc act aat aaa gga atg gcg cct cag gcg aat              891
Val Leu Gly Asn Gly Ser Thr Asn Lys Gly Met Ala Pro Gln Ala Asn
                 80                  85                  90 cta gtc ttc caa tct atc atg gat agc ggt ggg gga ctt gga gga cta              939
Leu Val Phe Gln Ser Ile Met Asp Ser Gly Gly Gly Leu Gly Gly Leu
                 95                 100                 105 cct tcg aat ctg caa acc tta ttc agc caa gca tac agt gct ggt gcc              987
Pro Ser Asn Leu Gln Thr Leu Phe Ser Gln Ala Tyr Ser Ala Gly Ala
                110                 115                 120 aga att cat aca aac tcc tgg gga gca gca gtg aat ggg gct tac aca             1035
Arg Ile His Thr Asn Ser Trp Gly Ala Ala Val Asn Gly Ala Tyr Thr
        125                 130                 135 aca gat tcc aga aat gtg gat gac tat gtg cgc aaa aat gat atg acg             1083
Thr Asp Ser Arg Asn Val Asp Asp Tyr Val Arg Lys Asn Asp Met Thr
140                 145                 150                 155 atc ctt ttc gct gcc ggg aat gaa gga ccg aac ggc gga acc atc agt             1131
Ile Leu Phe Ala Ala Gly Asn Glu Gly Pro Asn Gly Gly Thr Ile Ser
                160                 165                 170 gca cca ggc aca gct aaa aat gca ata aca gtc gga gct acg gaa aac             1179
Ala Pro Gly Thr Ala Lys Asn Ala Ile Thr Val Gly Ala Thr Glu Asn
        175                 180                 185 ctc cgc cca agc ttt ggg tct tat gcg gac aat atc aac cat gtg gca             1227
Leu Arg Pro Ser Phe Gly Ser Tyr Ala Asp Asn Ile Asn His Val Ala
            190                 195                 200 cag ttc tct tca cgt gga cca aca aag gat gga cgg atc aaa ccg gat             1275
Gln Phe Ser Ser Arg Gly Pro Thr Lys Asp Gly Arg Ile Lys Pro Asp
205                 210                 215 gtc atg gca ccg gga acg ttc ata cta tca gca aga tct tct ctt gca             1323
Val Met Ala Pro Gly Thr Phe Ile Leu Ser Ala Arg Ser Ser Leu Ala
220                 225                 230                 235 ccg gat tcc tcc ttc tgg gcg aac cat gac agt aaa tat gca tac atg             1371
Pro Asp Ser Ser Phe Trp Ala Asn His Asp Ser Lys Tyr Ala Tyr Met
                240                 245                 250 ggt gga acg tcc atg gct aca ccg atc gtt gct gga aac gtg gca cag             1419
Gly Gly Thr Ser Met Ala Thr Pro Ile Val Ala Gly Asn Val Ala Gln
        255                 260                 265 ctt cgt gag cat ttt gtg aaa aac aga ggc atc aca cca aag cct tct             1467
Leu Arg Glu His Phe Val Lys Asn Arg Gly Ile Thr Pro Lys Pro Ser
            270                 275                 280 cta tta aaa gcg gca ctg att gcc ggt gca gct gac atc ggc ctt ggc             1515
Leu Leu Lys Ala Ala Leu Ile Ala Gly Ala Ala Asp Ile Gly Leu Gly
285                 290                 295 tac ccg aac ggt aac caa gga tgg gga cga gtg aca ttg gat aaa tcc             1563
Tyr Pro Asn Gly Asn Gln Gly Trp Gly Arg Val Thr Leu Asp Lys Ser
300                 305                 310                 315 ctg aac gtt gcc tat gtg aac gag tcc agt tct cta tcc acc agc caa             1611
Leu Asn Val Ala Tyr Val Asn Glu Ser Ser Ser Leu Ser Thr Ser Gln
                320                 325                 330 aaa gcg acg tac tcg ttt act gct act gcc ggc aag cct ttg aaa atc             1659
Lys Ala Thr Tyr Ser Phe Thr Ala Thr Ala Gly Lys Pro Leu Lys Ile
        335                 340                 345 tcc ctg gta tgg tct gat gcc cct gcg agc aca act gct tcc gta acg             1707
```

-continued

```
Ser Leu Val Trp Ser Asp Ala Pro Ala Ser Thr Thr Ala Ser Val Thr
        350                 355                 360 ctt gtc aat gat ctg gac ctt gtc att acc gct cca aat ggc aca cag      1755
Leu Val Asn Asp Leu Asp Leu Val Ile Thr Ala Pro Asn Gly Thr Gln
        365                 370                 375 tat gta gga aat gac ttt act tcg cca tac aat gat aac tgg gat ggc      1803
Tyr Val Gly Asn Asp Phe Thr Ser Pro Tyr Asn Asp Asn Trp Asp Gly
380                 385                 390                 395 cgc aat aac gta gaa aat gta ttt att aat gca cca caa agc ggg acg      1851
Arg Asn Asn Val Glu Asn Val Phe Ile Asn Ala Pro Gln Ser Gly Thr
                400                 405                 410 tat aca att gag gta cag gct tat aac gta ccg gtt gga cca cag acc      1899
Tyr Thr Ile Glu Val Gln Ala Tyr Asn Val Pro Val Gly Pro Gln Thr
            415                 420                 425 ttc tcg ttg gca att gtg aat taa                                      1923
Phe Ser Leu Ala Ile Val Asn
                430

<210> SEQ ID NO 4
<211> LENGTH: 434
<212> TYPE: PRT
<213> ORGANISM: Bacillus sp. KSM-KP43

<400> SEQUENCE: 4

Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Thr Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Ala Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
```

```
                260                 265                 270
Val Lys Asn Arg Gly Ile Thr Pro Lys Pro Ser Leu Leu Lys Ala Ala
            275                 280                 285

Leu Ile Ala Gly Ala Ala Asp Ile Gly Leu Gly Tyr Pro Asn Gly Asn
            290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Thr Ala Ser Val Thr Leu Val Asn Asp Leu
            355                 360                 365

Asp Leu Val Ile Thr Ala Pro Asn Gly Thr Gln Tyr Val Gly Asn Asp
            370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 5
<211> LENGTH: 26
<212> TYPE: DNA
<213> ORGANISM: Artificial
<220> FEATURE:
<223> OTHER INFORMATION: Oligonculeotide as PCR primer 310-1480Nhe

<400> SEQUENCE: 5
aatgaggcta gccgtagttt ataggg                                          26

<210> SEQ ID NO 6
<211> LENGTH: 25
<212> TYPE: DNA
<213> ORGANISM: Artificial
<220> FEATURE:
<223> OTHER INFORMATION: Oligonculeotide as PCR primer 310-1480Nhe-R

<400> SEQUENCE: 6
ctacggctag cctcattatt ggagg                                           25

<210> SEQ ID NO 7
<211> LENGTH: 30
<212> TYPE: DNA
<213> ORGANISM: Artificial
<220> FEATURE:
<223> OTHER INFORMATION: Oligonculeotide as PCR primer TS-Xba down

<400> SEQUENCE: 7
gaattaatat ggtctagagt cgagacaagg                                      30

<210> SEQ ID NO 8
<211> LENGTH: 20
<212> TYPE: DNA
<213> ORGANISM: Artificial
<220> FEATURE:
<223> OTHER INFORMATION: Oligonculeotide as PCR primer 310-2690

<400> SEQUENCE: 8
```
tataacttta acagatgggg                                              20

<210> SEQ ID NO 9
<211> LENGTH: 25
<212> TYPE: DNA
<213> ORGANISM: Artificial
<220> FEATURE:
<223> OTHER INFORMATION: Oligonculeotide as PCR primer Rep48X
<220> FEATURE:
<221> NAME/KEY: misc_feature
<222> LOCATION: (10)..(12)
<223> OTHER INFORMATION: n stands for any base

<400> SEQUENCE: 9
cttgaatttn nnaaggctga aagag                                        25

<210> SEQ ID NO 10
<211> LENGTH: 25
<212> TYPE: DNA
<213> ORGANISM: Artificial
<220> FEATURE:
<223> OTHER INFORMATION: Oligonculeotide as PCR primer Rep48X-R
<220> FEATURE:
<221> NAME/KEY: misc_feature
<222> LOCATION: (14)..(16)
<223> OTHER INFORMATION: n stands for any base

<400> SEQUENCE: 10
ctctttcagc cttnnnaaat tcaag                                        25

<210> SEQ ID NO 11
<211> LENGTH: 23
<212> TYPE: DNA
<213> ORGANISM: Artificial
<220> FEATURE:
<223> OTHER INFORMATION: Oligonculeotide as PCR primer Rep262X
<220> FEATURE:
<221> NAME/KEY: misc_feature
<222> LOCATION: (10)..(12)
<223> OTHER INFORMATION: n stands for any base

<400> SEQUENCE: 11
cgtttgtctn nnttggagga agg                                          23

<210> SEQ ID NO 12
<211> LENGTH: 23
<212> TYPE: DNA
<213> ORGANISM: Artificial
<220> FEATURE:
<223> OTHER INFORMATION: Oligonculeotide as PCR primer Rep262X-R
<220> FEATURE:
<221> NAME/KEY: misc_feature
<222> LOCATION: (12)..(14)
<223> OTHER INFORMATION: n stands for any base

<400> SEQUENCE: 12
ccttcctcca annnagacaa acg                                          23

<210> SEQ ID NO 13
<211> LENGTH: 3150
<212> TYPE: DNA
<213> ORGANISM: Bacillus sp. KSM-S237
<220> FEATURE:
<221> NAME/KEY: CDS
<222> LOCATION: (573)..(3044)
<220> FEATURE:
<221> NAME/KEY: sig_peptide
<222> LOCATION: (573)..(659)
<220> FEATURE:
<221> NAME/KEY: mat_peptide
<222> LOCATION: (660)..()

```
<400> SEQUENCE: 13
gatttgccga tgcaacaggc ttatatttag aggaaatttc ttttttaaatt gaatacggaa      60 taaaatcagg taaacaggtc ctgatttttat tttttttgagt tttttagaga actgaagatt     120
gaaataaaag tagaagacaa aggacataag aaaattgcat tagttttaat tatagaaaac     180 gccttttat aattatttat acctagaacg aaaatactgt ttcgaaagcg gtttactata      240
aaaccttata ttccggctct ttttttaaaac aggggggtaaa aattcactct agtattctaa      300
tttcaacatg ctataataaa tttgtaagac gcaatatgca tctctttttt tacgatatat      360
gtaagcggtt aaccttgtgc tatatgccga tttaggaagg ggggtagatt gagtcaagta      420
gtaataatat agataactta taagttgttg agaagcagga gagcatctgg gttactcaca      480
agttttttta aaactttaac gaaagcactt tcggtaatgc ttatgaattt agctatttga      540
ttcaattact ttaaaaatat ttaggaggta at atg atg tta aga aag aaa aca       593
                                   Met Met Leu Arg Lys Lys Thr
                                                    -25 aag cag ttg att tct tcc att ctt att tta gtt tta ctt cta tct tta       641
Lys Gln Leu Ile Ser Ser Ile Leu Ile Leu Val Leu Leu Leu Ser Leu
   -20              -15                  -10 ttt ccg gca gct ctt gca gca gaa gga aac act cgt gaa gac aat ttt       689
Phe Pro Ala Ala Leu Ala Ala Glu Gly Asn Thr Arg Glu Asp Asn Phe
 -5              -1  1               5                  10 aaa cat tta tta ggt aat gac aat gtt aaa cgc cct tct gag gct ggc       737
Lys His Leu Leu Gly Asn Asp Asn Val Lys Arg Pro Ser Glu Ala Gly
             15                  20                  25 gca tta caa tta caa gaa gtc gat gga caa atg aca tta gta gat caa       785
Ala Leu Gln Leu Gln Glu Val Asp Gly Gln Met Thr Leu Val Asp Gln
         30                  35                  40 cat gga gaa aaa att caa tta cgt gga atg agt aca cac gga tta cag       833
His Gly Glu Lys Ile Gln Leu Arg Gly Met Ser Thr His Gly Leu Gln
     45                  50                  55 tgg ttt cct gag atc ttg aat gat aac gca tac aaa gct ctt tct aac       881
Trp Phe Pro Glu Ile Leu Asn Asp Asn Ala Tyr Lys Ala Leu Ser Asn
 60                  65                  70 gat tgg gat tcc aat atg att cgt ctt gct atg tat gta ggt gaa aat       929
Asp Trp Asp Ser Asn Met Ile Arg Leu Ala Met Tyr Val Gly Glu Asn
 75                  80                  85                  90 ggg tac gct aca aac cct gag tta atc aaa caa aga gtg att gat gga       977
Gly Tyr Ala Thr Asn Pro Glu Leu Ile Lys Gln Arg Val Ile Asp Gly
                 95                 100                 105 att gag tta gcg att gaa aat gac atg tat gtt att gtt gac tgg cat      1025
Ile Glu Leu Ala Ile Glu Asn Asp Met Tyr Val Ile Val Asp Trp His
             110                 115                 120 gtt cat gcg cca ggt gat cct aga gat cct gtt tat gca ggt gct aaa      1073
Val His Ala Pro Gly Asp Pro Arg Asp Pro Val Tyr Ala Gly Ala Lys
         125                 130                 135 gat ttc ttt aga gaa att gca gct tta tac cct aat aat cca cac att      1121
Asp Phe Phe Arg Glu Ile Ala Ala Leu Tyr Pro Asn Asn Pro His Ile
     140                 145                 150 att tat gag tta gcg aat gag ccg agt agt aat aat ggt gga gca      1169
Ile Tyr Glu Leu Ala Asn Glu Pro Ser Ser Asn Asn Gly Gly Ala
 155                 160                 165                 170 ggg att ccg aat aac gaa gaa ggt tgg aaa gcg gta aaa gaa tat gct      1217
Gly Ile Pro Asn Asn Glu Glu Gly Trp Lys Ala Val Lys Glu Tyr Ala
                 175                 180                 185 gat cca att gta gaa atg tta cgt aaa agc ggt aat gca gat gac aac      1265
Asp Pro Ile Val Glu Met Leu Arg Lys Ser Gly Asn Ala Asp Asp Asn
             190                 195                 200
```

```
att atc att gtt ggt agt cca aac tgg agt cag cgt ccg gac tta gca    1313
Ile Ile Ile Val Gly Ser Pro Asn Trp Ser Gln Arg Pro Asp Leu Ala
        205                 210                 215 gct gat aat cca att gat gat cac cat aca atg tat act gtt cac ttc    1361
Ala Asp Asn Pro Ile Asp Asp His His Thr Met Tyr Thr Val His Phe
    220                 225                 230 tac act ggt tca cat gct gct tca act gaa agc tat ccg tct gaa act    1409
Tyr Thr Gly Ser His Ala Ala Ser Thr Glu Ser Tyr Pro Ser Glu Thr
235                 240                 245                 250 cct aac tct gaa aga gga aac gta atg agt aac act cgt tat gcg tta    1457
Pro Asn Ser Glu Arg Gly Asn Val Met Ser Asn Thr Arg Tyr Ala Leu
                255                 260                 265 gaa aac gga gta gcg gta ttt gca aca gag tgg gga acg agt caa gct    1505
Glu Asn Gly Val Ala Val Phe Ala Thr Glu Trp Gly Thr Ser Gln Ala
            270                 275                 280 agt gga gac ggt ggt cct tac ttt gat gaa gca gat gta tgg att gaa    1553
Ser Gly Asp Gly Gly Pro Tyr Phe Asp Glu Ala Asp Val Trp Ile Glu
        285                 290                 295 ttt tta aat gaa aac aac att agc tgg gct aac tgg tct tta acg aat    1601
Phe Leu Asn Glu Asn Asn Ile Ser Trp Ala Asn Trp Ser Leu Thr Asn
    300                 305                 310 aaa aat gaa gta tct ggt gca ttt aca cca ttc gag tta ggt aag tct    1649
Lys Asn Glu Val Ser Gly Ala Phe Thr Pro Phe Glu Leu Gly Lys Ser
315                 320                 325                 330 aac gca acc aat ctt gac cca ggt cca gat cat gtg tgg gca cca gaa    1697
Asn Ala Thr Asn Leu Asp Pro Gly Pro Asp His Val Trp Ala Pro Glu
                335                 340                 345 gaa tta agt ctt tct gga gaa tat gta cgt gct cgt att aaa ggt gtg    1745
Glu Leu Ser Leu Ser Gly Glu Tyr Val Arg Ala Arg Ile Lys Gly Val
            350                 355                 360 aac tat gag cca atc gac cgt aca aaa tac acg aaa gta ctt tgg gac    1793
Asn Tyr Glu Pro Ile Asp Arg Thr Lys Tyr Thr Lys Val Leu Trp Asp
        365                 370                 375 ttt aat gat gga acg aag caa gga ttt gga gtg aat tcg gat tct cca    1841
Phe Asn Asp Gly Thr Lys Gln Gly Phe Gly Val Asn Ser Asp Ser Pro
    380                 385                 390 aat aaa gaa ctt att gca gtt gat aat gaa aac aac act ttg aaa gtt    1889
Asn Lys Glu Leu Ile Ala Val Asp Asn Glu Asn Asn Thr Leu Lys Val
395                 400                 405                 410 tcg gga tta gat gta agt aac gat gtt tca gat ggc aac ttc tgg gct    1937
Ser Gly Leu Asp Val Ser Asn Asp Val Ser Asp Gly Asn Phe Trp Ala
                415                 420                 425 aat gct cgt ctt tct gcc aac ggt tgg gga aaa agt gtt gat att tta    1985
Asn Ala Arg Leu Ser Ala Asn Gly Trp Gly Lys Ser Val Asp Ile Leu
            430                 435                 440 ggt gct gag aag ctt aca atg gat gtt att gtt gat gaa cca acg acg    2033
Gly Ala Glu Lys Leu Thr Met Asp Val Ile Val Asp Glu Pro Thr Thr
        445                 450                 455 gta gct att gcg gcg att cca caa agt agt aaa agt gga tgg gca aat    2081
Val Ala Ile Ala Ala Ile Pro Gln Ser Ser Lys Ser Gly Trp Ala Asn
    460                 465                 470 cca gag cgt gct gtt cga gtg aac gcg gaa gat ttt gtc cag caa acg    2129
Pro Glu Arg Ala Val Arg Val Asn Ala Glu Asp Phe Val Gln Gln Thr
475                 480                 485                 490 gac ggt aag tat aaa gct gga tta aca att aca gga gaa gat gct cct    2177
Asp Gly Lys Tyr Lys Ala Gly Leu Thr Ile Thr Gly Glu Asp Ala Pro
                495                 500                 505 aac cta aaa aat atc gct ttt cat gaa gaa gat aac aat atg aac aac    2225
Asn Leu Lys Asn Ile Ala Phe His Glu Glu Asp Asn Asn Met Asn Asn
            510                 515                 520
```

```
atc att ctg ttc gtg gga act gat gca gct gac gtt att tac tta gat    2273
Ile Ile Leu Phe Val Gly Thr Asp Ala Ala Asp Val Ile Tyr Leu Asp
        525                 530                 535 aac att aaa gta att gga aca gaa gtt gaa att cca gtt gtt cat gat    2321
Asn Ile Lys Val Ile Gly Thr Glu Val Glu Ile Pro Val Val His Asp
540                 545                 550 cca aaa gga gaa gct gtt ctt cct tct gtt ttt gaa gac ggt aca cgt    2369
Pro Lys Gly Glu Ala Val Leu Pro Ser Val Phe Glu Asp Gly Thr Arg
555                 560                 565                 570 caa ggt tgg gac tgg gct gga gag tct ggt gtg aaa aca gct tta aca    2417
Gln Gly Trp Asp Trp Ala Gly Glu Ser Gly Val Lys Thr Ala Leu Thr
                575                 580                 585 att gaa gaa gca aac ggt tct aac gcg tta tca tgg gaa ttt gga tat    2465
Ile Glu Glu Ala Asn Gly Ser Asn Ala Leu Ser Trp Glu Phe Gly Tyr
        590                 595                 600 cca gaa gta aaa cct agt gat aac tgg gca aca gct cca cgt tta gat    2513
Pro Glu Val Lys Pro Ser Asp Asn Trp Ala Thr Ala Pro Arg Leu Asp
                605                 610                 615 ttc tgg aaa tct gac ttg gtt cgc ggt gag aat gat tat gta gct ttt    2561
Phe Trp Lys Ser Asp Leu Val Arg Gly Glu Asn Asp Tyr Val Ala Phe
        620                 625                 630 gat ttc tat cta gat cca gtt cgt gca aca gaa ggc gca atg aat atc    2609
Asp Phe Tyr Leu Asp Pro Val Arg Ala Thr Glu Gly Ala Met Asn Ile
635                 640                 645                 650 aat tta gta ttc cag cca cct act aac ggg tat tgg gta caa gca cca    2657
Asn Leu Val Phe Gln Pro Pro Thr Asn Gly Tyr Trp Val Gln Ala Pro
                655                 660                 665 aaa acg tat acg att aac ttt gat gaa tta gag gaa gcg aat caa gta    2705
Lys Thr Tyr Thr Ile Asn Phe Asp Glu Leu Glu Glu Ala Asn Gln Val
        670                 675                 680 aat ggt tta tat cac tat gaa gtg aaa att aac gta aga gat att aca    2753
Asn Gly Leu Tyr His Tyr Glu Val Lys Ile Asn Val Arg Asp Ile Thr
                685                 690                 695 aac att caa gat gac acg tta cta cgt aac atg atg atc att ttt gca    2801
Asn Ile Gln Asp Asp Thr Leu Leu Arg Asn Met Met Ile Ile Phe Ala
            700                 705                 710 gat gta gaa agt gac ttt gca ggg aga gtc ttt gta gat aat gtt cgt    2849
Asp Val Glu Ser Asp Phe Ala Gly Arg Val Phe Val Asp Asn Val Arg
715                 720                 725                 730 ttt gag ggg gct gct act act gag ccg gtt gaa cca gag cca gtt gat    2897
Phe Glu Gly Ala Ala Thr Thr Glu Pro Val Glu Pro Glu Pro Val Asp
                735                 740                 745 cct ggc gaa gag acg cca cct gtc gat gag aag gaa gcg aaa aaa gaa    2945
Pro Gly Glu Glu Thr Pro Pro Val Asp Glu Lys Glu Ala Lys Lys Glu
        750                 755                 760 caa aaa gaa gca gag aaa gaa gag aaa gaa gca gta aaa gaa gaa aag    2993
Gln Lys Glu Ala Glu Lys Glu Glu Lys Glu Ala Val Lys Glu Glu Lys
        765                 770                 775 aaa gaa gct aaa gaa gaa aag aaa gca gtc aaa aat gag gct aag aaa    3041
Lys Glu Ala Lys Glu Glu Lys Lys Ala Val Lys Asn Glu Ala Lys Lys
        780                 785                 790 aaa taatctatta aactagttat agggttatct aaaggtctga tgtagatctt         3094
Lys
795 ttagataacc ttttcttgc ataactggac acagagttgt tattaaagaa agtaag       3150
```

<210> SEQ ID NO 14
<211> LENGTH: 3332
<212> TYPE: DNA
<213> ORGANISM: Bacillus sp. KSM-64

```
<220> FEATURE:
<221> NAME/KEY: CDS
<222> LOCATION: (610)..(3075)
<220> FEATURE:
<221> NAME/KEY: sig_peptide
<222> LOCATION: (610)..(696)
<220> FEATURE:
<221> NAME/KEY: mat_peptide
<222> LOCATION: (697)..()

<400> SEQUENCE: 14
agtacttacc attttagagt caaaagatag aagccaagca ggatttgccg atgcaaccgg      60
cttatattta gagggaattt ctttttaaat tgaatacgga ataaaatcag gtaaacaggt     120
cctgatttta ttttttttgaa ttttttttgag aactaaagat tgaaatagaa gtagaagaca    180
acggacataa gaaaattgta ttagttttaa ttatagaaaa cgcttttcta taattattta     240
tacctagaac gaaaatactg tttcgaaagc ggtttactat aaaaccttat attccggctc     300
ttttttttaaa caggggggtga aaattcactc tagtattcta atttcaacat gctataataa   360
atttgtaaga cgcaatatac atctttttt tatgatattt gtaagcggtt aaccttgtgc      420
tatatgccga tttaggaagg gggtagattg agtcaagtag tcataattta gataacttat    480
aagttgttga gaagcaggag agaatctggg ttactcacaa gttttttaaa acattatcga    540
aagcactttc ggttatgctt atgaatttag ctatttgatt caattacttt aataatttta    600
ggaggtaat atg atg tta aga aag aaa aca aag cag ttg att tct tcc att      651
         Met Met Leu Arg Lys Lys Thr Lys Gln Leu Ile Ser Ser Ile
                -25             -20
ctt att tta gtt tta ctt cta tct tta ttt ccg aca gct ctt gca gca        699
Leu Ile Leu Val Leu Leu Leu Ser Leu Phe Pro Thr Ala Leu Ala Ala
-15             -10              -5              -1  1
gaa gga aac act cgt gaa gac aat ttt aaa cat tta tta ggt aat gac        747
Glu Gly Asn Thr Arg Glu Asp Asn Phe Lys His Leu Leu Gly Asn Asp
            5               10              15
aat gtt aaa cgc cct tct gag gct ggc gca tta caa tta caa gaa gtc        795
Asn Val Lys Arg Pro Ser Glu Ala Gly Ala Leu Gln Leu Gln Glu Val
        20              25              30
gat gga caa atg aca tta gta gat caa cat gga gaa aaa att caa tta        843
Asp Gly Gln Met Thr Leu Val Asp Gln His Gly Glu Lys Ile Gln Leu
    35              40              45
cgt gga atg agt aca cac gga tta caa tgg ttt cct gag atc ttg aat        891
Arg Gly Met Ser Thr His Gly Leu Gln Trp Phe Pro Glu Ile Leu Asn
50              55              60              65
gat aac gca tac aaa gct ctt gct aac gat tgg gaa tca aat atg att        939
Asp Asn Ala Tyr Lys Ala Leu Ala Asn Asp Trp Glu Ser Asn Met Ile
                70              75              80
cgt cta gct atg tat gtc ggt gaa aat ggc tat gct tca aat cca gag        987
Arg Leu Ala Met Tyr Val Gly Glu Asn Gly Tyr Ala Ser Asn Pro Glu
            85              90              95
tta att aaa agc aga gtc att aaa gga ata gat ctt gct att gaa aat       1035
Leu Ile Lys Ser Arg Val Ile Lys Gly Ile Asp Leu Ala Ile Glu Asn
        100             105             110
gac atg tat gtc atc gtt gat tgg cat gta cat gca cct ggt gat cct       1083
Asp Met Tyr Val Ile Val Asp Trp His Val His Ala Pro Gly Asp Pro
    115             120             125
aga gat ccc gtt tac gct gga gca gaa gat ttc ttt aga gat att gca       1131
Arg Asp Pro Val Tyr Ala Gly Ala Glu Asp Phe Phe Arg Asp Ile Ala
130             135             140             145
gca tta tat cct aac aat cca cac att att tat gag tta gcg aat gag       1179
Ala Leu Tyr Pro Asn Asn Pro His Ile Ile Tyr Glu Leu Ala Asn Glu
                150             155             160
```

```
cca agt agt aac aat aat ggt gga gct ggg att cca aat aat gaa gaa    1227
Pro Ser Ser Asn Asn Asn Gly Gly Ala Gly Ile Pro Asn Asn Glu Glu
            165                 170                 175 ggt tgg aat gcg gta aaa gaa tac gct gat cca att gta gaa atg tta    1275
Gly Trp Asn Ala Val Lys Glu Tyr Ala Asp Pro Ile Val Glu Met Leu
            180                 185                 190 cgt gat agc ggg aac gca gat gac aat att atc att gtg ggt agt cca    1323
Arg Asp Ser Gly Asn Ala Asp Asp Asn Ile Ile Ile Val Gly Ser Pro
        195                 200                 205 aac tgg agt cag cgt cct gac tta gca gct gat aat cca att gat gat    1371
Asn Trp Ser Gln Arg Pro Asp Leu Ala Ala Asp Asn Pro Ile Asp Asp
210                 215                 220                 225 cac cat aca atg tat act gtt cac ttc tac act ggt tca cat gct gct    1419
His His Thr Met Tyr Thr Val His Phe Tyr Thr Gly Ser His Ala Ala
                230                 235                 240 tca act gaa agc tat ccg cct gaa act cct aac tct gaa aga gga aac    1467
Ser Thr Glu Ser Tyr Pro Pro Glu Thr Pro Asn Ser Glu Arg Gly Asn
            245                 250                 255 gta atg agt aac act cgt tat gcg tta gaa aac gga gta gca gta ttt    1515
Val Met Ser Asn Thr Arg Tyr Ala Leu Glu Asn Gly Val Ala Val Phe
            260                 265                 270 gca aca gag tgg gga act agc caa gca aat gga gat ggt ggt cct tac    1563
Ala Thr Glu Trp Gly Thr Ser Gln Ala Asn Gly Asp Gly Gly Pro Tyr
        275                 280                 285 ttt gat gaa gca gat gta tgg att gag ttt tta aat gaa aac aac att    1611
Phe Asp Glu Ala Asp Val Trp Ile Glu Phe Leu Asn Glu Asn Asn Ile
290                 295                 300                 305 agc tgg gct aac tgg tct tta acg aat aaa aat gaa gta tct ggt gca    1659
Ser Trp Ala Asn Trp Ser Leu Thr Asn Lys Asn Glu Val Ser Gly Ala
                310                 315                 320 ttt aca cca ttc gag tta ggt aag tct aac gca aca agt ctt gac cca    1707
Phe Thr Pro Phe Glu Leu Gly Lys Ser Asn Ala Thr Ser Leu Asp Pro
            325                 330                 335 ggg cca gac caa gta tgg gta cca gaa gag tta agt ctt tct gga gaa    1755
Gly Pro Asp Gln Val Trp Val Pro Glu Glu Leu Ser Leu Ser Gly Glu
            340                 345                 350 tat gta cgt gct cgt att aaa ggt gtg aac tat gag cca atc gac cgt    1803
Tyr Val Arg Ala Arg Ile Lys Gly Val Asn Tyr Glu Pro Ile Asp Arg
        355                 360                 365 aca aaa tac acg aaa gta ctt tgg gac ttt aat gat gga acg aag caa    1851
Thr Lys Tyr Thr Lys Val Leu Trp Asp Phe Asn Asp Gly Thr Lys Gln
370                 375                 380                 385 gga ttt gga gtg aat gga gat tct cca gtt gaa gat gta gtt att gag    1899
Gly Phe Gly Val Asn Gly Asp Ser Pro Val Glu Asp Val Val Ile Glu
                390                 395                 400 aat gaa gcg ggc gct tta aaa ctt tca gga tta gat gca agt aat gat    1947
Asn Glu Ala Gly Ala Leu Lys Leu Ser Gly Leu Asp Ala Ser Asn Asp
            405                 410                 415 gtt tct gaa ggt aat tac tgg gct aat gct cgt ctt tct gcc gac ggt    1995
Val Ser Glu Gly Asn Tyr Trp Ala Asn Ala Arg Leu Ser Ala Asp Gly
            420                 425                 430 tgg gga aaa agt gtt gat att tta ggt gct gaa aaa ctt act atg gat    2043
Trp Gly Lys Ser Val Asp Ile Leu Gly Ala Glu Lys Leu Thr Met Asp
        435                 440                 445 gtg att gtt gat gag ccg acc acg gta tca att gct gca att cca caa    2091
Val Ile Val Asp Glu Pro Thr Thr Val Ser Ile Ala Ala Ile Pro Gln
450                 455                 460                 465 ggg cca tca gcc aat tgg gtt aat cca aat cgt gca att aag gtt gag    2139
Gly Pro Ser Ala Asn Trp Val Asn Pro Asn Arg Ala Ile Lys Val Glu
                470                 475                 480
```

```
                                                            -continued cca act aat ttc gta ccg tta gga gat aag ttt aaa gcg gaa tta act       2187
Pro Thr Asn Phe Val Pro Leu Gly Asp Lys Phe Lys Ala Glu Leu Thr
            485                 490                 495 ata act tca gct gac tct cca tcg tta gaa gct att gcg atg cat gct       2235
Ile Thr Ser Ala Asp Ser Pro Ser Leu Glu Ala Ile Ala Met His Ala
500                 505                 510 gaa aat aac aac atc aac aac atc att ctt ttt gta gga act gaa ggt       2283
Glu Asn Asn Asn Ile Asn Asn Ile Ile Leu Phe Val Gly Thr Glu Gly
        515                 520                 525 gct gat gtt atc tat tta gat aac att aaa gta att gga aca gaa gtt       2331
Ala Asp Val Ile Tyr Leu Asp Asn Ile Lys Val Ile Gly Thr Glu Val
530                 535                 540                 545 gaa att cca gtt gtt cat gat cca aaa gga gaa gct gtt ctt cct tct       2379
Glu Ile Pro Val Val His Asp Pro Lys Gly Glu Ala Val Leu Pro Ser
                550                 555                 560 gtt ttt gaa gac ggt aca cgt caa ggt tgg gac tgg gct gga gag tct       2427
Val Phe Glu Asp Gly Thr Arg Gln Gly Trp Asp Trp Ala Gly Glu Ser
            565                 570                 575 ggt gtg aaa aca gct tta aca att gaa gaa gca aac ggt tct aac gcg       2475
Gly Val Lys Thr Ala Leu Thr Ile Glu Glu Ala Asn Gly Ser Asn Ala
        580                 585                 590 tta tca tgg gaa ttt gga tac cca gaa gta aaa cct agt gat aac tgg       2523
Leu Ser Trp Glu Phe Gly Tyr Pro Glu Val Lys Pro Ser Asp Asn Trp
595                 600                 605 gca aca gct cca cgt tta gat ttc tgg aaa tct gac ttg gtt cgc ggt       2571
Ala Thr Ala Pro Arg Leu Asp Phe Trp Lys Ser Asp Leu Val Arg Gly
610                 615                 620                 625 gaa aat gat tat gta act ttt gat ttc tat cta gat cca gtt cgt gca       2619
Glu Asn Asp Tyr Val Thr Phe Asp Phe Tyr Leu Asp Pro Val Arg Ala
                630                 635                 640 aca gaa ggc gca atg aat atc aat tta gta ttc cag cca cct act aac       2667
Thr Glu Gly Ala Met Asn Ile Asn Leu Val Phe Gln Pro Pro Thr Asn
            645                 650                 655 ggg tat tgg gta caa gca cca aaa acg tat acg att aac ttt gat gaa       2715
Gly Tyr Trp Val Gln Ala Pro Lys Thr Tyr Thr Ile Asn Phe Asp Glu
        660                 665                 670 tta gag gaa gcg aat caa gta aat ggt tta tat cac tat gaa gtg aaa       2763
Leu Glu Glu Ala Asn Gln Val Asn Gly Leu Tyr His Tyr Glu Val Lys
675                 680                 685 att aac gta aga gat att aca aac att caa gat gac acg tta cta cgt       2811
Ile Asn Val Arg Asp Ile Thr Asn Ile Gln Asp Asp Thr Leu Leu Arg
690                 695                 700                 705 aac atg atg atc att ttt gca gat gta gaa agt gac ttt gca ggg aga       2859
Asn Met Met Ile Ile Phe Ala Asp Val Glu Ser Asp Phe Ala Gly Arg
                710                 715                 720 gtc ttt gta gat aat gtt cgt ttt gag ggg gct gct act act gag ccg       2907
Val Phe Val Asp Asn Val Arg Phe Glu Gly Ala Ala Thr Thr Glu Pro
            725                 730                 735 gtt gaa cca gag cca gtt gat cct ggc gaa gag acg ccg cct gtc gat       2955
Val Glu Pro Glu Pro Val Asp Pro Gly Glu Glu Thr Pro Pro Val Asp
        740                 745                 750 gag aag gaa gcg aaa aaa gaa caa aaa gaa gca gag aaa gaa gag aaa       3003
Glu Lys Glu Ala Lys Lys Glu Gln Lys Glu Ala Glu Lys Glu Glu Lys
755                 760                 765 gaa gca gta aaa gaa gaa aag aaa gaa gct aaa gaa gaa aag aaa gca       3051
Glu Ala Val Lys Glu Glu Lys Lys Glu Ala Lys Glu Glu Lys Lys Ala
770                 775                 780                 785 atc aaa aat gag gct acg aaa aaa taatctaata aactagttat agggttatct      3105
Ile Lys Asn Glu Ala Thr Lys Lys
                790
```

```
aaaggtctga tgcagatctt ttagataacc ttttttttgca taactggaca tagaatggtt    3165
attaaagaaa gcaaggtgtt tatacgatat taaaaaggta gcgattttaa attgaaacct    3225
ttaataatgt cttgtgatag aatgatgaag taatttaaga gggggaaacg aagtgaaaac    3285
ggaaatttct agtagaagaa aaacagacca agaaatactg caagctt                  3332
```